United States Patent
Eaton (10) Patent No.: US 12,251,377 B2
(45) Date of Patent: Mar. 18, 2025

(54) ANTICOAGULANT COMPOSITIONS AND USES THEREOF

(71) Applicant: University of Rochester, Rochester, NY (US)

(72) Inventor: Michael P. Eaton, Rochester, NY (US)

(73) Assignee: University of Rochester, Rochester, NY (US)

( * ) Notice: Subject to any disclaimer, the term of this patent is extended or adjusted under 35 U.S.C. 154(b) by 794 days.

(21) Appl. No.: 17/436,270

(22) PCT Filed: Feb. 19, 2020

(86) PCT No.: PCT/US2020/018717
§ 371 (c)(1),
(2) Date: Sep. 3, 2021

(87) PCT Pub. No.: WO2020/180489
PCT Pub. Date: Sep. 10, 2020

(65) Prior Publication Data
US 2022/0175748 A1    Jun. 9, 2022

Related U.S. Application Data (60) Provisional application No. 62/814,454, filed on Mar. 6, 2019.

(51) Int. Cl.
| | | |
|---|---|---|
| *A61K 31/4439* | (2006.01) | |
| *A61K 39/395* | (2006.01) | |
| *A61P 7/02* | (2006.01) | |
| *C07K 16/44* | (2006.01) | |

(52) U.S. Cl.
CPC .... *A61K 31/4439* (2013.01); *A61K 39/39583* (2013.01); *A61P 7/02* (2018.01); *C07K 16/44* (2013.01)

(58) Field of Classification Search
CPC .................................................. A61K 31/4439
USPC ....................................................... 514/338
See application file for complete search history.

(56) References Cited

FOREIGN PATENT DOCUMENTS

| | | |
|---|---|---|
| CN | 109010249 A | 12/2018 |
| CN | 109125274 A | 1/2019 |
| WO | 2006103206 A2 | 10/2006 |
| WO | 2008009638 A2 | 1/2008 |
| WO | 2010055022 A1 | 5/2010 |

OTHER PUBLICATIONS

Reilly et al., Idarucizumab, a Specific Reversal Agent for Dabigatran: Mode of Action, Pharmacokinetics and Pharmacodynamics, and Safety and Efficacy in Phase 1 Subjects, The American Journal of Medicine, vol. 129, No. 11A, pp. S64-S72 (Nov. 2016).*
Nagakura et al., "Selective tissue factor/factor VIIa Inhibitor, ER-410660, and its prodrug, E5539, have anti-venous and anti-arterial thombotic effects with a low risk of bleeding," Thrombosis Research (2013); 132: 271-279.
Schiele et al., "A specific antidote for dabigatran: functional and structural characterization," Blood (2013); 121(18): 3554-3562.

* cited by examiner

*Primary Examiner* — Mark L Shibuya
*Assistant Examiner* — Rilla Marie Samsell
(74) *Attorney, Agent, or Firm* — Fox Rothschild LLP

(57) ABSTRACT

The invention relates to novel compositions managing or inhibiting blood clotting and related uses.

13 Claims, 4 Drawing Sheets

ANTICOAGULANT COMPOSITIONS AND USES THEREOF

CROSS REFERENCE TO RELATED APPLICATION

This application is the national phase of International Patent Application No. PCT/US20/18717 filed on Feb. 19, 2020, which claims priority to U.S. Provisional Application No. 62/814,454 filed on Mar. 6, 2019. The content of the application is incorporated herein by reference in its entirety.

FIELD OF THE INVENTION

The invention relates to novel compositions that inhibit blood clotting and related uses.

BACKGROUND OF THE INVENTION

Anticoagulants, agents that prevent coagulation and stop blood from clotting, are widely used as a medication for thrombotic disorders such as primary and secondary prevention of deep vein thrombosis, pulmonary embolism, myocardial infarctions and strokes in those who are predisposed. Yet, currently, no single anticoagulant exists which can adequately fulfill ideal pharmacological requirements for cardiopulmonary bypass. Traditionally Heparin has been the preferred anticoagulant during bypass, but Heparin has multiple disadvantages and is contraindications in patients suffering from Heparin Induced Thrombocytopenia (HIT). While the direct thrombin inhibitor (DTI) bivalirudin has been used successfully for human bypass, published experience shows that excessive postoperative bleeding is common, and multiple cases report the formation of clots within the bypass circuit, especially in areas of stasis, exposing a dangerously narrow therapeutic window. There is a need for anticoagulants for cardiopulmonary bypass.

SUMMARY OF INVENTION

This invention addresses the need mentioned above in a number of aspects.

In one aspect, the invention provides a liquid parenteral pharmaceutical composition comprising (i) about 2 µg/ml to 20 mg/ml (e.g., about 3 µg/ml to about 18 mg/ml, about 200 µg/ml to about 17 mg/ml, about 400 µg/ml to about 4 mg/ml, about 2 to about 18 mg/ml, about 3 to about 17 mg/ml, and about 5 to about 10 mg/ml) dabigatran or a pharmaceutically acceptable salt thereof. The composition can further comprise (ii) about 0 to about 0.2 M or N (e.g., about 20 µM to about 0.1 M, about 1 mM to about 0.1 M, about 0.01 M to about 0.08 M, about 0.05 M to about 0.15 M, about 0.075 M, and about 0.1 M) of an acidulant; and (iii) about 0 to about 75% (weight/volume) (e.g., about 10 to about 60% and about 15 to about 50%) of a polar aprotic agent, based on the total volume of the composition.

In a second aspect, the invention provides a method for managing or inhibiting blood coagulation during a procedure in a subject. The method comprises administering parenterally to the subject or the blood thereof an effective amount of dabigatran so that the blood dabigatran concentration is about 200 ng/ml to about 30,000 ng/ml (e.g., about 250, about 300, about 500, about 2,000, about 2,400, about 3,000, about 4,000, about 4,800, about 5,000, about 6,000, about 7,000, about 8,000, about 9,000, about 10,000 and about 20,000 ng/ml). In some examples, the blood dabigatran concentration is about 2,400 ng/ml to about 20,000 ng/ml or about 9,600 ng/ml to about 20,000 ng/ml. In the method, the administering step can comprise administering to the subject or the blood thereof the liquid pharmaceutical composition described above, which comprises about 2 µg/ml to about 20 mg/ml dabigatran or a pharmaceutically acceptable salt thereof.

Example of the procedure mentioned above include a cardiopulmonary bypass procedure or an extracorporeal circulation procedure. In that case, the dabigatran-containing composition can be administered to the subject before or during the procedure. In particular, the dabigatran-containing composition can be administered to a prime volume of the subject in vitro in a heart-lung machine for the procedure. Preferably, a first dose of the dabigatran-containing composition is administered to the subject first before the procedure, and then a second dose of the dabigatran-containing composition is added to the prime volume. When needed, the method can further comprise administering to the subject an effective amount of a second anticoagulant. Examples of the second anticoagulant include a direct-acting Factor Xa inhibitor, such as rivaroxaban, apixaban, fondaparinux, edoxaban, and betrixaban. Also if there is a need to stop or control unwanted bleeding events, the method can include administer to the subject a reversal agent or antidote that is able to stop such anticoagulant-related bleeding events when they occur. The reversal agent or antidote neutralizes the activity of the anticoagulant compound. Examples include an antibody or an antigen-binding portion thereof that specifically binds to dabigatran. Examples of such anti-dabigatran antibody include Idarucizumab.

In a third aspect, the invention features a method for making the composition described above. The method includes (a) mixing dabigatran or a pharmaceutically acceptable salt thereof with an acidulant solution (e.g., about 0.01 to about 0.2 M, about 0.05 to about 0.15 M, about 0.075, about 0.08, about 0.09, about 0.1, about 0.11, about 0.12, about 0.13, about 0.14, or about 0.15 M HCl or other) to obtain a first solution; and (b) combining the first solution with an aprotic agent (e.g., a polar aprotic agent) to obtain a second solution thereby obtaining the composition. Examples of the polar aprotic agent include dimethyl sulfoxide (DMSO), dimethylacetamide (DMAc or DMA), 1-methyl-2-pyrrolidinone (NMP), or a combination thereof.

In a fourth aspect, the invention provides a kit comprising (i) the liquid parenteral pharmaceutical composition described above and (ii) a reversal agent mentioned above, e.g., an antibody that specifically binds to dabigatran or a pharmaceutically acceptable salt thereof, such as idarucizumab.

In a fifth aspect, the invention encompasses a composition for transfusion into a patient. The composition comprises (i) blood or a component thereof and (ii) about 200 ng to about 30,000 ng dabigatran or a pharmaceutically acceptable salt per ml of the blood or a component thereof (e.g., about 250, about 300, about 500, about 2,000, about 2,400, about 3,000, about 4,000, about 4,800, about 5,000, about 6,000, about 7,000, about 8,000, about 9,000, about 10,000 and about 20,000 ng/ml). This composition encompasses blood or plasma that contains high-concentration dabigatran during cardiopulmonary bypass.

The details of one or more embodiments of the invention are set forth in the description below. Other features, objectives, and advantages of the invention will be apparent from the description and from the claims.

BRIEF DESCRIPTION OF THE DRAWINGS

FIGS. 2A and 2B are diagrams showing: (FIG. 2A) Clotting time (R) measured by TEG in the presence of Dabigatran. (FIG. 2B) Time for the clot formation in the Chandler Loop System. Data are shown as mean±SEM from N=6 donors measured in duplicate. Statistical significance vs. control (no drug). Single symbol * indicate P<0.05.

DETAILED DESCRIPTION OF THE INVENTION

The present invention relates to pharmaceutical compositions comprising dabigatran as an active agent, process of preparation thereof, and method of using the same. Particularly the invention relates to a liquid pharmaceutical composition comprising dabigatran, or pharmaceutically acceptable salts, esters, derivatives, hydrates, polymorphs, and solvates thereof, process of preparation and method of using the same.

Dabigatran

Dabigatran is a potent thrombin inhibitor that can be used for example for the post-operative prevention of deep vein thromboses and in stroke prevention, particularly for preventing strokes in patients with atrial fibrillation. However, using dabigatran for managing or inhibiting blood coagulation during procedures, such as cardiopulmonary bypass (CPB) or an extracorporeal circulation procedure, has proven to be difficult due to its low water solubility. The liquid dabigatran pharmaceutical composition disclosed herein can be further dissolved or solubilized in intravenous diluents rapidly. Accordingly, it can be used for managing or inhibiting blood coagulation, e.g., during a CPB procedure or an extracorporeal circulation procedure in a subject.

As used herein, the term "dabigatran" unless indicated otherwise, refers to dabigatran in its free base form, or as a prodrug dabigatran etexilate, or as a pharmaceutically acceptable salt, or esters, or hydrates or solvates thereof. Preferably, dabigatran is in the base form. Examples of dabigatrans include BIBR 953 (CAS number 211914-51-1), BIBR 1048 (a prodrug dabigatran etexilate), or pharmaceutically acceptable acid addition salt thereof, such as in the form of dabigatran etexilate methanesulfonate (mesylate) salt. Dabigatran Etexilate, which is also referred to as "BIBR 1048" is a synthetic, non-peptide competitive, rapidly acting oral direct thrombin inhibitor. The IUPAC names of BIBR 953 and BIBR 1048 are ethyl 3-{[(2-{[(4-{N'-[(hexyloxy)carbonyl]carbamimidoyl}phenyl)amino]methyl}-1-methyl-1H-benzimidazol-5-yl)carbonyl](2-pyridinyl)amino}propanoate and 3-[(2-{[4-(hexyloxycarbonylamino-imino-methyl)-phenylamino]-methyl}-1-methyl-1H-benzimidazole-5-carbonyl)-pyridine-2-yl-amino]-propionic acid ethyl ester.

Dabigatran etexilate is currently marketed as PRADAXA immediate release oral capsule to reduce the risk of stroke and systemic embolism in patients with non-valvular atrial fibrillation. This oral formulation contains dabigatran etexilate in the form of the mesylate salt. Each PRADAXA capsule contains the following inactive ingredients: acacia, dimethicone, hypromellose, hydroxypropylcellulose, tartaric acid, carragenan, potassium chloride, talc, titanium dioxide, and gelatin. Taken orally, a PRADAXA capsule generally can achieve a steady-state blood concentration of about 180 ng/ml, which is not sufficient to manage or inhibit blood coagulation during CPB.

Dabigatran etexilate mesylate has a solubility in water of only 1.8 mg/ml. The solubility is strongly pH-dependent and increased in the acidic environment. Although this may not pose a bioavailability problem for oral compositions since the active ingredient's solubility is greatly increased in a patient's stomach, parenteral uses (e.g., intravenous or subcutaneous injection) cannot fulfill ideal pharmacological requirements for CPB bypass. There is therefore a need for parenteral pharmaceutical compositions of the active ingredient dabigatran that provide bioavailability of the active ingredient to achieve blood concentrations higher than 180 ng/ml, such as about 200 ng/ml to 30,000 ng/ml.

The present invention addresses this need by providing liquid solution compositions that comprises dabigatran up to about 20 mg/ml and are suitable for parenteral uses. Another advantageous property of the pharmaceutical composition according to the invention is its suitability for all patients, i.e., including those whose gastric pH is raised as a result of normal physiological variability, illness, or medication with drugs which increase the gastric pH (e.g., pantoprazole).

Compositions and Method of Making

This invention provides a liquid pharmaceutical composition that contains dabigatran at a high concentration. The composition is suitable for preparing various pharmaceutical compositions for parenteral uses. In particular, it may be used to prepare liquid composition for mixing with a patient blood to achieve high blood dabigatran concentration, e.g., about 200 ng/ml to about 30,000 ng/ml as mentioned above. The composition described herein can further include another agent or agents other than dabigatran. For example, another blood clotting inhibitor/anti-coagulation agent/anti-platelet agent can also be included as well.

In addition to dabigatran and other agents described herein, the composition can further include one or more other pharmaceutically active compounds that provide an additional prophylactic or therapeutic benefit to a patient, e.g., a patient of an invasive surgical procedure or a patent otherwise at risk for, having or previously had cerebral ischemia and/or reperfusion injury associated with cerebral ischemia. For example, the compositions can include another compound described herein.

A composition of this invention can further include one or more pharmaceutically acceptable buffers, carriers, and excipients, which can provide a desirable feature to the composition including, but not limited to, enhanced administration of the composition to a patient, enhanced circulating half-life of dabigatran agent and/or a second active agent (such as another blood clotting inhibitor/anti-coagulation agent/anti-platelet agent), enhanced compatibility of dabigatran and other active agents with patient blood chemistry, enhanced storage of the composition, and/or enhanced delivery and/or efficacy of dabigatran and/or another agent upon administration to a patient.

Accordingly, the composition may further include a stabilizing agent, such as mannitol, histidine, lysine, glycine, sucrose, fructose, trehalose, lactose or a mixture thereof. The composition can optionally contain a bulking agent, such as mannitol, glycine, lactose, sucrose, trehalose, dextran, hydroxyethyl starch, ficoll or gelatin. The composition can optionally contain a solubilizing agent or surfactant, such as cetrimide, docusate sodium, glyceryl monooleate, sodium lauryl sulfate, or sorbitan esters. The solubilizing agent or surfactant may optionally be a polyoxyethylenesorbitan fatty acid ester. Polyoxyethylenesorbitan fatty acid esters are also referred to as polysorbates, e.g., polysorbate 80 (polyoxyethylene sorbitan monooleate, Tween 80), polysorbate 40 and polysorbate 20. Polysorbates, such as polysorbate 80, are commercially available, for example, from Sigma, St. Louis, Mo.

The composition can optionally comprise a buffer, such as acetates, citrates, tartrates, lactates, succinates, or phosphates. The composition can optionally contain a tonicity agent, such as glycerin, lactose, mannitol, dextrose, sodium chloride, sodium sulfate or sorbitol. The composition can optionally contain an antioxidant, such as acetone, sodium bisulfite, bisulfite sodium, butylated hydroxy anisole, butylated hydroxy toluene, cysteine, cysteinate HCl, dithionite sodium, gentisic acid, gentisic acid ethanolamine, glutamate monosodium, formaldehyde sulfoxylate sodium, metabisulfite potassium, metabisulfite sodium, monothioglycerol, propyl gallate, sulfite sodium, thioglycolate sodium, or ascorbic acid.

The above-described active ingredients can be typically formulated into pharmaceutical dosage forms to provide an easily controllable dosage of the drug and to give the patient an elegant and easily handleable product.

Also provided is a method of preparing a liquid parenteral pharmaceutical composition describe herein. The method comprises mixing dabigatran or a pharmaceutically acceptable salt thereof with an acidulant or pH adjusting agent to obtain a first solution; and then combining the first solution with an aprotic agent/solvent (such as a polar aprotic agent/solvent) to obtain a second solution thereby obtaining the composition. This liquid composition is suitable for parenteral uses and can be further diluted as described herein with a diluent suitable for parenteral uses. The composition can optionally contain a stabilizing agent, a buffer, a tonicity agent or an antioxidant.

Suitable pH adjusting agents and buffering agents that may be used in the invention include phosphate buffer, citrate buffer, sodium carbonate, sodium bicarbonate, tartarate, benzoate, acetate, borate, lactic acid, glutaric acid, malic acid, succinic acid and carbonic acid, alkali or alkaline earth salt of one of these acids, Tris, meglumine, amino acids such as arginine, glycine, histidine and lysine; sodium hydroxide, potassium hydroxide, ammonium carbonate, hydrochloric acid, citric acid, phosphoric acid and the like.

Polar aprotic solvents suitable for the present methods include polar aprotic solvents well known in the art, and the examples include, but are not limit to, DMAc, dimethyl formamide (DMF), dDMSO, NMP, acetonitrile (ACN), and the like. In one embodiment, the solvents in use of the present invention are selected from dimethyl acetamide and dimethyl sulfoxide.

Uses

The composition described herein can be used in methods for managing or inhibiting blood coagulation. In addition, the composition can also be used for preventing or reducing blood loss, e.g., perioperative blood loss; methods for preventing or reducing injury associated with ischemia (e.g., reperfusion injury associated with ischemia); and/or a systemic inflammatory response (SIR) in a patient, especially associated with surgery. The surgery can be, e.g., a cardiothoracic surgery, (e.g., CPB or coronary artery bypass grafting); orthopedic surgery (e.g., hip or knee replacement or bone fracture); liver surgery; kidney surgery; procedures that utilize extracorporeal circulation or dialysis; and any other procedure which can result in perioperative blood loss.

In CPB, large cannulae are inserted into the great vessels of a patient to permit mechanical pumping and oxygenation of the blood using a membrane oxygenator. The blood is returned to the patient without flowing through the lungs, which are hypoperfused during this procedure. The peripheral circulating volume is increased by an extracorporeal circuit, i.e., the CPB circuit, which requires "priming" with a CPB priming fluid (such as donor blood and saline mixtures) to fill the extracorporeal circuit. CPB has been extensively used in a variety of procedures performed for over half a century with successful outcomes. The interaction between artificial surfaces, blood cells, blood proteins, damaged vascular endothelium, and extravascular tissues, such as bone, disturbs hemostasis and frequently activates a contact activation system (CAS), which can result in a variety of disruptions in the blood and vasculature. Such disruption leads to excess perioperative bleeding, which then requires immediate blood transfusion.

A consequence of circulating whole blood through an extracorporeal circuit in CPB can also include the systemic inflammatory response, which is initiated by contact activation of the coagulation and complement systems. Indeed, much of the morbidity and mortality associated with seemingly mechanically successful CPB surgical procedures is the result of the effects of activating coagulation, fibrinolysis, or complement systems. Such activation can damage the pulmonary system, leading to adult respiratory distress syndrome (ARDS), impairment of kidney and splanchnic circulation, and induction of a general coagulopathy leading to blood loss and the need for transfusions. In addition to the dangers of perioperative blood loss, additional pathologies associated with SIR include neurocognitive deficits, stroke, renal failure, acute myocardial infarct, and cardiac tissue damage.

Use of the compositions described herein alone or in combination with additional agents (such as various anti-thrombolytic agents or anti-fibrinolytic agents) can improve these treatments and lead to reduction and/or amelioration of the undesirable symptoms that can occur.

Routes

A composition of this invention can be administered by any suitable route known to those of skill in the art that ensures bioavailability in the circulation. Administration can be achieved by parenteral routes of administration, including, but not limited to, intravenous (IV), intramuscular (IM), intradermal, subcutaneous (SC), and intraperitoneal (IP) injections. In certain embodiments, administration is by a bypass machine, perfuser, infiltrator or catheter. In certain embodiments, the composition is administered by injection, by a subcutaneously implantable pump or by a depot preparation, in doses that achieve a therapeutic effect. Suitable dosage forms are further described in Remington's Pharmaceutical Sciences, 1990, 17$^{th}$ ed., Mack Publishing Company, Easton, Pa., a standard reference text in this field, which is incorporated herein by reference in its entirety.

The effective amount of dabigatran to be administered alone or in combination with another agent may vary depending on the type of surgery, condition of the patient, age of the patient, patient's weight, medical history of the patient, the manner of administration and the judgment of the prescribing physician. It will be appreciated by one of skill in the art that the degree of blood anticoagulation can be monitored by laboratory values such as prothrombin time (PT) and partial thromboplastin time (PTT). Determination of an effective amount is well within the capabilities of those skilled in the art, especially in light of the detailed disclosure provided herein.

The administration of the composition of this invention may be repeated intermittently. The composition can be administered alone or in combination with other drugs, for example, other presurgical drugs such as antibiotics or anesthetics.

For parenteral administration, the composition/agent can be injected intravenously, intramuscularly, intraperitoneally, or subcutaneously. Intravenous administration is preferred. Typically, compositions for intravenous administration are solutions in sterile isotonic aqueous buffer. Other pharmaceutically acceptable carriers include, but are not limited to, sterile water, saline solution, and buffered saline (including buffers like phosphate or acetate), alcohol, vegetable oils, polyethylene glycols, gelatin, lactose, amylose, magnesium stearate, talc, silicic acid, paraffin, etc. Where necessary, the composition can also include a solubilizing agent and a local anaesthetic such as lidocaine to ease pain at the site of the injection, preservatives, stabilizers, wetting agents, emulsifiers, salts, lubricants, etc. as long as they do not react deleteriously with the active compounds. Similarly, the composition can comprise conventional excipients, e.g., pharmaceutically acceptable organic or inorganic carrier substances suitable for parenteral, enteral or intranasal application which do not deleteriously react with the active compounds. Generally, the ingredients will be supplied either separately or mixed together in unit dosage form, for example, in a hermetically sealed container such as an ampoule or sachette indicating the quantity of active agent in activity units. Where the composition is to be administered by infusion, it can be dispensed with an infusion bottle containing sterile pharmaceutical grade "water for injection" or saline. Where the composition is to be administered by injection, an ampoule of sterile water for injection or saline can be provided so that the ingredients can be mixed prior to administration.

Timing

A composition of this invention can be administered to a patient before, during, and/or after an event that causes or is associated with blood clotting, e.g., a surgical procedure, or an ischemic event, e.g., a cerebral ischemic attack, in connection with another disorder or event described herein. The patient is generally a human, but may also be a non-human mammal. Human patients include adults, e.g., patients between ages 19-25, 26-40, 41-55, 56-75, and 76 and older, and pediatric patients, e.g., patients between ages 0-2, 3-6, 7-12, and 13-18.

A composition of this invention and/or an additional therapeutically agent (e.g., another blood clotting inhibitor) can be administered perioperatively; that is, before surgery, after surgery and/or during surgery, or any combination as described herein. For example, if the half-life of an agent is long (24-48 hours), the agent can be administered as one dose within 48 (or 24) hours prior to surgery with repeated doses during or after surgery. Agents with shorter half-lives can be given sooner before surgery and then be administered during or after surgery. In some patients, and some circumstances, the treating physician may decide to suspend pre-operative treatment, and only start administration postoperatively, e.g., 48 hours after surgery, after wound closure to assure that no bleeding has occurred in the field (no open blood vessels) before starting anti-clotting therapy. Such immediate postoperative administration of a blood clotting inhibitor is within the scope of the invention.

In a preferred embodiment, a composition of this invention can be administered to a patient in the immediate pre-operative period. For example, in a procedure involving CPB, a composition described herein can be administered to a patient as an initial loading dose, e.g., an effective amount over the course of a convenient time, such as 10 minutes, after induction of anesthesia and before cannulation of the great vessels. Then, at induction of anesthesia, a second dose of the composition can be injected into the CPB priming fluid ("pump prime volume"). The patient can then be placed on a continuous and controlled intravenous infusion dose for the duration of the surgical procedure, and after the procedure if indicated.

Administration in the perioperative period can be a single, one time dose or multiple doses of the composition of this invention. In certain embodiments, perioperative administration can be continuous, uninterrupted administration of the composition (e.g., a continuous infusion or transdermal delivery). In another embodiment, perioperative administration is single or multiple discreet administration(s) within the perioperative time frame (e.g., a single dose given within the perioperative period or multiple doses given within the perioperative period). In one embodiment, the composition can be administered within about 6 days, 5 days, 4 days, 3 days, 2 days or 1 day perioperatively. In another embodiment, the composition can be administered within about 48 hours, 36 hours, 24 hours, 12 hours, 8 hours, 6 hours or 1 hour perioperatively.

The composition can be administered during surgery, for example, contemporaneously with the use or discontinuation of cardiopulmonary bypass. Administration can be continued long term for example, after surgery, following discharge from hospital and for six months, one year or longer post-operatively. In certain embodiments, when the patient is on chronic blood clotting inhibitor therapy prior to surgery, the blood clotting inhibitor is not discontinued pre-operatively, in contrast to standard practice.

Other Anti-Coagulants

The methods described herein can further include administration of another agent or agents other than dabigatran. For example, another blood clotting inhibitor/anti-coagulation agent or anti-platelet agent can also be administered to the patient.

Such blood clotting inhibitor/anti-coagulation agent can be any drug, agent or pharmaceutical composition that prevents or inhibits blood clotting. The inhibitor/agent can act by preventing or inhibiting blood clot formation by any of a variety of mechanisms including reduction of blood clotting factors or reducing platelet activation or aggregation, or mitigating the effects of instigating factors, such as inflammation or stress. The blood clotting inhibitor can also act by breaking down or dissolving a blood clot after formation. It will be apparent to those of skill in the art that there are several classes of blood clotting inhibitor, including antiplatelet agents, thrombolytic enzymes, aggregation inhibitors, glycoprotein IIb/IIIa inhibitors, glycosaminoglycans, thrombin inhibitors, anticoagulants, heparins, low molecular weight heparins, coumarins, indandione derivatives and tissue plasminogen activators. See, The Physicians' Desk Reference (56.sup.th ed., 2002) Medical Economics; Mosby's Drug Consult, 2002, Elsevier Science; Goodman and Gilman's The Pharmacologic Basis of Therapeutics, (9$^{th}$. 1996) Pergamon Press; Drug Facts and Comparisons, updated monthly, September, 2002, Facts and Comparisons, Wolters Kluwer Company, St. Louis, Mo.

For the purposes of this invention, any drug, agent or pharmaceutical composition that prevents or inhibits the formation of blood clots or dissolves or breaks down a blood clot is suitable for use in the present invention. Such a blood clotting inhibitor can be, for example, cilostazol (PLETAL, OTSUKA), clopidogrel (PLAVIX, SANOFI), ticlopidine (TICLID, SYNTEX), tirofiban (AGGRASTAT, MERCK), eptifibatide (INTEGRILIN, COR THERAPEUTICS), abciximab (REOPRO, ELI LILLY), anagrelide (AGRYLIN), dipyridamole (PERSANTIN, BOEHRINGER INGELHEIM), aspirin (ECOTR, and others), dipyridamole/aspirin (AGGRENOX, BOEHRINGER INGELHEIM), dalteparin (FRAGMIN), enoxaparin (LOVENOX, AVENTIS), tinzaparin (INNOHE, DUPONT), heparin (various), danaparoid (ORGANON, ORGANON), antithrombin III (THROMBATE, BAYER), lepirudin (REFLUDAN), argatroban (ACOVA), bivalirudin (ANGIOMAX), warfarin (COUMADIN, DUPONT) anisidione (MIRADON, SCHERING), alteplase (ACTIVASE, GENETECH), reteplase (RETAVASE, BOEHRINGER MANNHEIM), tenecteplase (TNKASE, GENENTECH), drotrecogin (XIGRIS, ELI LILLY), anistreplase (EMINASE), streptokinase (STREPTASE), urokinase (ABBOKINASE. ABBOTT) and combinations thereof.

It will be appreciated by those of skill in the art that blood clotting inhibitors can be used for the treatment of occluded catheters and for the maintenance of patency of vascular access devices. Heparin, urokinase, streptokinase and alteplase are generally employed for such uses.

Reversal Agents

Blood coagulation or clotting is a biological mechanism to stop bleeding. A major adverse effect of anticoagulant therapy is unwanted bleeding events. It is therefore desirable to provide a reversal agent or antidote that is able to stop such anticoagulant-related bleeding events when they occur (Zikria and Ansell, Current Opinion in Hematology 2009, 16(5): 347-356). One way to achieve this is by neutralizing the activity of the anticoagulant compound present in the patient after administration. Examples include an antibody or an antigen-binding portion thereof that specifically binds to dabigatran. Examples of such anti-dabigatran include Idarucizumab and others described in US20150210778, which is incorporated by reference. Accordingly, the invention provides a safer mode for anticoagulation during bypass than Bivalirudin, Hirudin, or Heparin alone.

Devices and Kits

Pharmaceutical compositions described herein can be administered with a medical device. The device can be designed with features such as portability, room temperature storage, and ease of use so that it can be used in emergency situations, e.g., by an untrained subject or by emergency personnel in the field, removed to medical facilities and other medical equipment. The device can include, e.g., one or more housings for storing the pharmaceutical compositions and can be configured to deliver one or more unit doses of the agent or agents. For example, the pharmaceutical composition can be administered with a medication infusion pump for delivering medication at a precise infusion rate; or with a variable flow implantable infusion apparatus for continuous drug delivery as disclosed in U.S. Pat. Nos. 4,447,233 and 4,447,224. Many other devices, implants, delivery systems, and modules are also known.

A composition described herein can be provided in a kit. In one embodiment, the kit includes (a) a container that contains the composition, and optionally (b) informational material. The informational material can be descriptive, instructional, marketing or other material that relates to the methods described herein and/or the use of the agents for therapeutic benefit. In an embodiment, the kit includes also includes another therapeutic agent or a reversal agent. For example, the kit includes a first container that contains the composition, and a second container that includes the reversal agent (such as anti-dabigatran antibody).

The informational material of the kits is not limited in its form. In one embodiment, the informational material can include information about production of the composition, concentration, date of expiration, batch or production site information, and so forth. In one embodiment, the informational material relates to methods of administering the composition, e.g., in a suitable dose, dosage form, or mode of administration (e.g., a dose, dosage form, or mode of administration described herein), to treat a subject who has or is at risk for blood clotting, e.g., a patient subjected to invasive surgical procedures, especially procedures requiring cardiopulmonary bypass. In one embodiment, the instructions provide a dosing regimen, dosing schedule, and/or route of administration of the composition, or the reversal agent. The information can be provided in a variety of formats, include printed text, computer readable material, video recording, or audio recording, or an information that provides a link or address to substantive material.

In addition to the composition, the kit can include other ingredients, such as a solvent or buffer, a stabilizer, or a preservative. The composition can be provided in any form, e.g., liquid, dried or lyophilized form, preferably substantially pure and/or sterile. When the agents are provided in a liquid solution, the liquid solution preferably is an aqueous solution. When the agents are provided as a dried form, reconstitution generally is by the addition of a suitable solvent and acidulant. The acidulant and solvent, e.g., an aprotic solvent, sterile water, or a buffer, can optionally be provided in the kit.

The kit can include one or more containers for the composition or compositions containing dabigatran. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both dabigatran and a second agent in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

Definitions

As used herein, a "liquid parenteral pharmaceutical formulation of dabigatran" refers to formulation or composition that contain dabigatran in dissolved or solubilized form and are intended to be used as such or upon further dilution in intravenous diluents.

A formulation or composition is "suitable for parenteral use" or "suitable for use as a parenteral formulation" if it is in a pharmaceutically acceptable form for parenteral administration. Thus, for example, for a liquid parenteral formulation, the particle content is sufficiently low, and the material is sufficiently sterile such that it is useful for parenteral administration. To be suitable for parenteral administration, the formulation is visibly clear, and the number of particles in the reconstituted liquid product is kept to a minimum. For example, less than 6,000, 5,000, 4,000 10-μm particles should be present in a volume of 1 mL solvent that includes 20 mg of dabigatran.

As used herein, the term "unit dose" or "unit dosage" refers to physically discrete units that contain a predetermined quantity of active ingredient calculated to produce a desired therapeutic effect. When a unit dose is administered parenterally, it is typically provided in the form of measured units in ampoules (or vials). The dosage to be administered may vary depending upon the physical characteristics of the patient, the severity of the patient's symptoms, and the means used to administer the drug. The specific dose for a given patient is usually set by the judgment of the attending physician. Dosages can be for example, about 5-500 mg or about 35-200 mg daily administered from an intravenous injection (IV).

As used herein, unless indicated otherwise, references to total weight of the pharmaceutical composition refers to the total weight of the active agent(s) and pharmaceutically acceptable carrier or excipient(s).

The term "aprotic solvent" or "aprotic agent" refers to a solvent molecule which can neither accept nor donate a proton, or a solution containing such agent/solvent. Typical aprotic solvents include, but are not limited to, acetone, acetonitrile, benzene, butanone, butyronitrile, carbon tetrachloride, chlorobenzene, chloroform, 1,2-dichloroethane, dichloromethane (DCM), diethyl ether, dimethylacetamide, N,N-dimethylformamide (DMF), DMSO, NMP, 1,4-dioxane, ethyl acetate, ethylene glycol dimethyl ether, hexane, N-methylpyrrolidone, pyridine, tetrahydrofuran (THF), and toluene. Certain aprotic solvents are polar solvents. Examples of polar aprotic solvents include, but are not limited to, acetone, acetonitrile, butanone, N,N-dimethylformamide, and dimethylsulfoxide. Certain aprotic solvents are non-polar solvents (e.g., non-polar organic solvents). Examples of nonpolar organic solvents include, but are not limited to, diethyl ether, aliphatic hydrocarbons, such as hexane, aromatic hydrocarbons, such as benzene and toluene, and halogenated hydrocarbons, such as carbon tetrachloride, DCM, and chloroform.

A "blood clotting inhibitor" or "anti-coagulant" refers to any drug, agent or pharmaceutical composition that can block, prevent or inhibit the formation of blood clots or dissolves or breaks down a blood clot. A blood clotting inhibitor can be any blood clotting inhibitor currently known to those of skill in the art or one later developed. The blood clotting inhibitor can be from any drug class of blood clotting inhibitors known to those of skill in the art including, but not limited to, antiplatelet agents, thrombolytic enzymes, aggregation inhibitors, glycoprotein IIb/IIIa inhibitors, glycosaminoglycans, thrombin inhibitors, anticoagulants, heparin, low molecular weight heparins, coumarins, indandione derivatives, tissue plasminogen activators and combinations thereof. The blood clotting inhibitors can be in any pharmaceutical dosage form and administered by any route known to those of skill in the art.

The blood clotting inhibitor can be a combination of two or more blood clotting inhibitors. Combinations of blood clotting inhibitors can include blood clotting inhibitors from more than one drug class as described herein. In addition, the combination of blood clotting inhibitors can include different routes of administration for each blood clotting inhibitor. The combination of blood clotting inhibitors can be administered simultaneously or contemporaneously. In addition, the combination of blood clotting inhibitors can be administered separately.

Anti-thrombolytic agents are agents that reduce or prevent dissolution of a blood clot, stabilize a blood clot, increase clotting and/or prevent abnormal amounts of blood loss such as hemorrhaging by maintaining, stabilizing or increasing a blood clot. The anti-thrombolytic agent can be an anti-fibrinolytic agent. Anti-fibrinolytic agents are agents that prevent or reduce the dissolution or breakdown of fibrin. Examples of anti-fibrinolytic agents include tranexamic acid (CYKLOKAPRON), epsilon amino caproic acid (AMICAR), aprotinin (TRASYOL), and combinations thereof. The anti-fibrinolytic activity of an agent may be determined by any in vitro clot lysis activity known in the art, such as the purified clot lysis assay described by Carlson, et al., Anal. Biochem. 168, 428-435 (1988) and its modified form described by Bennett, W. F. et al., 1991, supra, the entire contents of which are hereby incorporated by reference.

The term "pharmaceutically acceptable" composition refers to a non-toxic carrier or excipient that may be administered to a patient, together with a blood clotting inhibitor and/or anti-thrombolytic agent described herein. The carrier or excipient is chosen to be compatible with the biological or pharmacological activity of the composition. The inhibitors and/or anti-thrombolytic agents described herein can be administered locally or systemically by any suitable means for delivery of an inhibitory amount of the inhibitor and/or anti-thrombolytic agent to a patient including but not limited to systemic administrations such as, for example, intravenous and inhalation. Parenteral administration is particularly preferred.

"Pharmaceutically acceptable excipient(s)" are components other than the active ingredient that are added to make a pharmaceutical formulation. Excipients may be added to facilitate manufacture, enhance stability, enhance product characteristics, enhance bioavailability, enhance patient acceptability, etc. Useful pharmaceutical excipients according to the present invention include diluents, binders, disintegrants, surfactants, glidant, lubricants, glidants/antiadherants; chelating agents; vehicles; bulking agents; stabilizers; preservatives and a combination thereof. It will be appreciated by A person skilled in the art that a particular excipient may act as both a binder and filler, or as a binder, filler and a disintegrant, or can have any other uses.

A "reversal agent" or "antidote" refers to a substance (e.g., a reagent, antibody, protein or a drug) that reverses the effect of anticoagulation (e.g., the reversal agent reverses the bleeding effected by the anticoagulant) that is present in a blood component of the patient if that substance is taken by or administered to the patient prior to obtaining the blood component from the patient. Such administration may be by any route including oral, parenteral, intravenous, intraperitoneal, intramuscular, subcutaneous, etc.

"Perioperative" refers to the time period before surgery (pre-operative), after surgery (post-operative), during surgery (intra-operative), and/or any combination as described herein. For example, a blood clotting inhibitor can be administered 48 hours perioperatively; that is, the blood clotting inhibitor can be administered 48 hours before surgery (pre-operatively), 48 hours after surgery (post-operative), during surgery (intra-operative) or any combination of these administration times. The administration during the perioperative period can be a single dose or multiple doses within the perioperative time period.

As used herein, the terms "subject" and "patient" are used interchangeably irrespective of whether the subject has or is currently undergoing any form of treatment. As used herein, the terms "subject" and "subjects" may refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgus monkey, chimpanzee, etc.) and a human) The subject may be a human or a non-human.

"Surgery" or "surgical" refers to any manual or operative methods or manipulations for the treatment or prevention of disease, injury or deformity. Surgery includes methods or manipulations conducted while a patient is under anesthesia, including local or general anesthesia. Surgery can be performed by a doctor, surgeon or dentist, generally in a hospital or other health care facility. Patients undergoing surgery can be hospitalized or ambulatory, e.g., out-patient surgery.

As used herein, the term "about" refers to within 10%, preferably within 5%, and more preferably within 1% of a given value or range. Alternatively, the term "about" refers to within an acceptable standard error of the mean, when considered by one of ordinary skill in the art.

Unless otherwise indicated or clear from the context, the term "antibody" as used herein may include immunoglobulins, whole antibodies and any antigen-binding fragments (i.e., "antigen-binding portions") or single chains thereof. An "antibody" refers, in one embodiment, to a glycoprotein comprising at least two heavy (H) chains and two light (L) chains inter-connected by disulfide bonds, or an antigen-binding fragment thereof. Each heavy chain is comprised of a heavy chain variable region (abbreviated herein as $V_H$) and a heavy chain constant region. In certain naturally occurring IgG, IgD and IgA antibodies, the heavy chain constant region is comprised of three domains, CH1, CH2 and CH3. In certain naturally occurring antibodies, each light chain is comprised of a light chain variable region (abbreviated herein as $V_L$) and a light chain constant region. The light chain constant region is comprised of one domain, $C_L$. The $V_H$ and $Y_L$ regions can be further subdivided into regions of hypervariability, termed complementarity determining regions (CDR), interspersed with regions that are more conserved, termed framework regions (FR). Each $V_H$ and $V_L$ is composed of three CDRs and four framework regions (FRs), arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

Antibodies typically bind specifically to their cognate antigen with high affinity, reflected by a dissociation constant ($K_D$) of $10^{-7}$ to $10^{-11}$ M or less. Any $K_D$ greater than about $10^{-6}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$M or less, preferably $10^{-8}$ M or less, even more preferably $5 \times 10^{-9}$ M or less, and most preferably between $10^{-8}$ M and $10^{-10}$ M or less, but does not bind with high affinity to unrelated antigens.

Unless otherwise indicated, an immunoglobulin may be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. Immunoglobulins, e.g., human IgG1, exist in several allotypes, which differ from each other in at most a few amino acids. Unless otherwise indicated, "antibody" may include, by way of example, monoclonal and polyclonal antibodies; chimeric and humanized antibodies; human and non-human antibodies; wholly synthetic antibodies; and single chain antibodies.

The term "prime volume" or "pump prime volume" refers to a fluid or solution used to remove air from a CPB circuit before a CPB procedure (also called priming) This de-airing process is done by priming the CPB circuit with such a fluid or solution or prime volume, generally consisting of a mixture of crystalloids and colloids. Priming causes haemodilution which improves flows during hypothermia. An anticoagulant can be added to the prime fluid/solution/volume. Depending on the pre-bypass haemoglobin and priming volume, addition of external blood may be required to maintain a target haematocrit on bypass (21%-24% in adults and 28%-30% in children). See. e.g., Sarkar et al., Indian J Anaesth. 2017 September; 61(9): 760-767, the content of which is incorporated by reference.

EXAMPLES

In the examples below, studies were carried out to examine effects of dabigatran on coagulation of human blood. The studies were approved by the Institutional Review Board (University of Rochester RSRB, Rochester, NY) and informed consent was obtained from all subjects. Six healthy non-pregnant donors between 18-70 years old were recruited for the study. Subjects were excluded from the recent infections, disorders of immune system, hematological disorders including prior history of clotting issues, malignancies. Current medications and herbal supplements were recorded. Standard phlebotomy procedures performed by trained personal were used to collect no more than 250 ml of whole blood in two months. The collected blood was anticoagulated with 0.109 M Na citrate and tested within four hours. Dabigatran was purchased from CLEARSYNTH (Ontario, Canada). The study was initiated in three steps: Effect of high-dose Dabigatran on coagulation of human blood in-vitro; Evaluation of the anticoagulant effect of Dabigatran in the Chandler Loop System; and Anticoagulation effect of Dabigatran in the Cardiopulmonary bypass circuit simulation.

Example 1 Effect of High-Dose Dabigatran on Coagulation of Human Blood In-Vitro

Goal: The goal of this study was to investigate the anticoagulant effect of high concentrations of the direct thrombin inhibitor Dabigatran on human blood in vitro, measured by thromboelastometry. Inventors also evaluated whether high concentrations of Dabigatran were reversible with clinically relevant concentrations of Idarucizumab.

Methods: Dabigatran (CLEARSYNTH, Catalog No. CS-O-03403; CAS number 211914-51-1) was initially dissolved in 0.1M HCL to 16.6 mg/ml, followed by diluting to 240 μg/ml, using 50% DMSO. Seven stock solutions were prepared: 240, 120, 60, 30, 15, 7.5, and 3.75 μl g/ml. Five μl of Dabigatran from the corresponding stock solutions and 5 μl of solvent (50% DMSO) were added into 990 μl of citrated blood to create the final concentrations of Dabigatran: 18.75, 37.5, 75, 150, 300, 600 and 1200 ng/ml. Concentrations were chosen with a wide distribution above and below normal concentrations found in patients (180 ng/ml). TEG 5000 (rapid TEG test) and ROTEM (ex-tem test) were used to measure anticoagulation and the corresponding reactive time (R) and coagulation time (CT) were recorded.

Figure 1A:
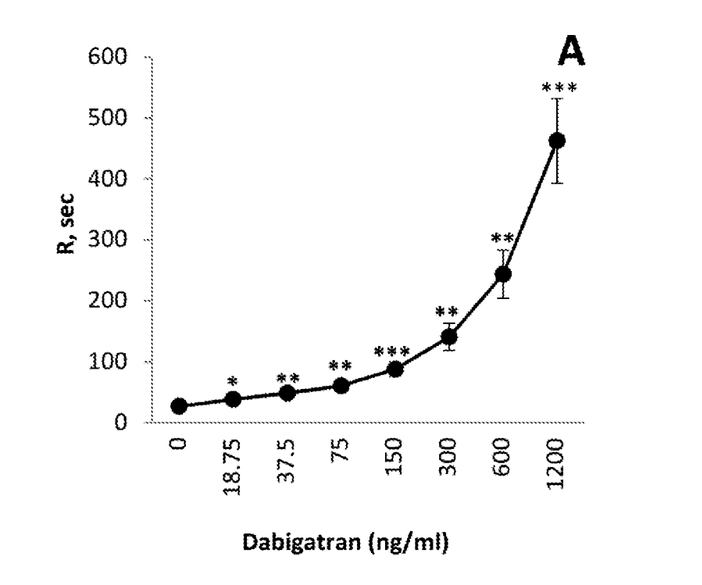
FIGS. 1A and 1B are diagrams showing clotting time (R) measured by thromboelastography (TEG) and (FIG. 1A) and coagulation time (CT) recorded by rotational thromboelastometry (ROTEM) (FIG. 1B). Data are shown as mean±standard error of the mean (SEM) from N=6 independent experiments (donors) measured in duplicate. Statistical significance vs. control. Single symbol * indicate P<0.05;  indicate P<0.01; * indicates P<0.001; **** indicates P<0.0001.
Figure 1B:
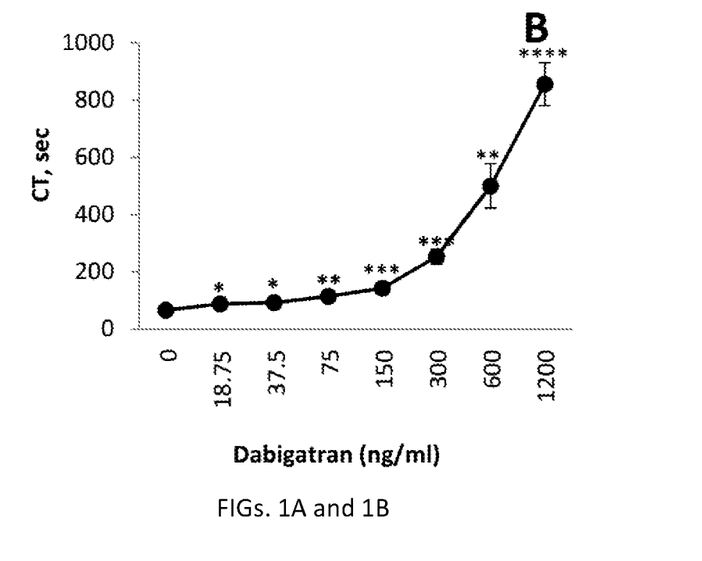

Results: Dabigatran prolonged R (FIG. 1A, N=6, *$p<0.05$ vs. 0 ng/ml) and CT (FIG. 1B) in a dose dependent manner. Anticoagulation effect of Dabigatran was successfully reversed with 125 μg/ml Idarucizumab, although 2-4 times normal plasma concentrations were required to reverse the highest concentrations of Dabigatran.

Example 2 Evaluation of the Anticoagulation Effect of Dabigatran in the Chandler Loop System Goal: In Chandler Loop System the moderate volumes of blood are perfused through PVC tubing used for CPB in a temperature controlled basin. This system is a simplest model for CPB. The system was used as an ex-vivo model allowing the assessment of the anticoagulant concentrations of Dabigatran. Idarucizumab was added to reverse the effect of Dabigatran after 2 hours of circulation.

Methods: Dabigatran was initially dissolved in 0.1 M HCL, followed by diluting 1:1 with DMSO/$H_2O$ to prepare four stock solutions: 3840, 1920, 960 and 480 mg/ml. From the corresponding stock solutions 175 μl of Dabigatran was added to 35 ml of citrated blood to create the final concentrations of Dabigatran: 2400, 4800, 9600 and 19200 ng/ml. TEG 5000 (rapid TEG test) was used to measure anticoagulation. Blood clotting was monitored for 120 minutes. Heparin was utilized as a positive anticoagulation control.

Figure 2A:
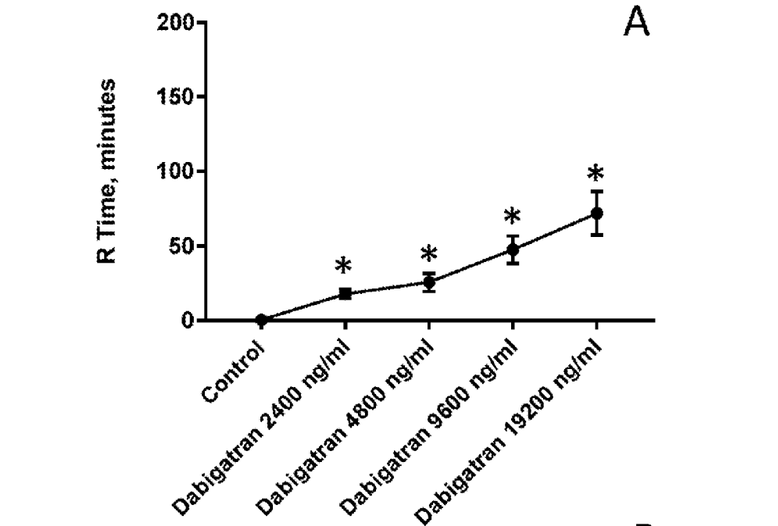
Figure 2B:
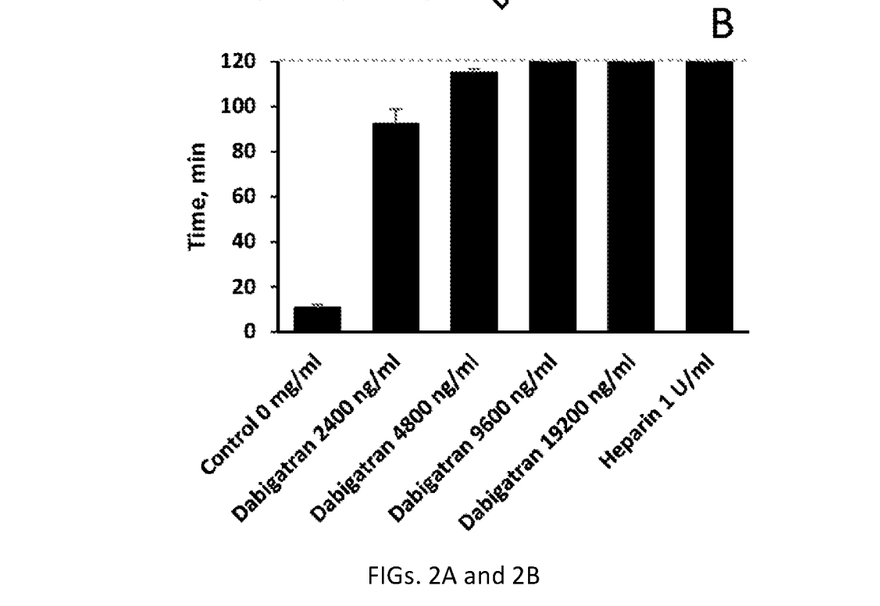
Figure 3:
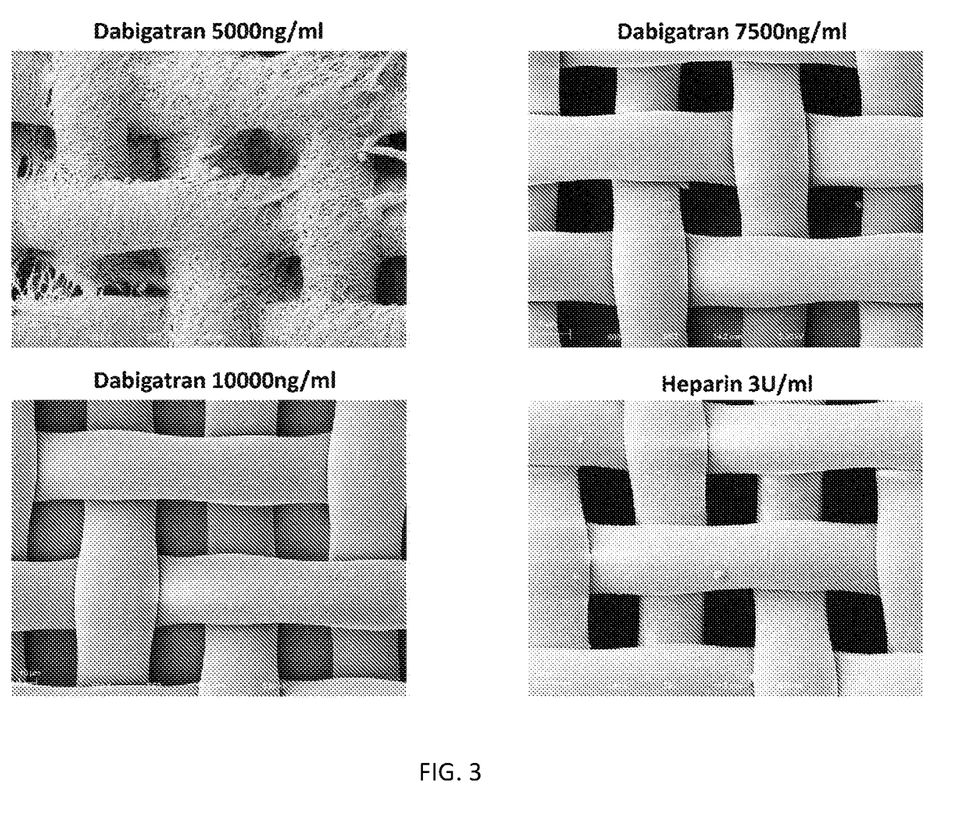
FIG. 3 is a set of photographs showing representative electron microscopy pictures (×500) of the filters obtained from the cardiopulmonary bypass circuits (arterio-venous loop) after 2 hours of blood perfusion.

Results: Dabigatran prolonged R time in a dose dependent manner (FIG. 2A). At 9600 and 19200 ng/ml Dabigatran prevented clot formation in blood from all six volunteers during 120 min of circulation in the Chandler loop (FIG. 2B). Idarucizumab effectively reversed the anticoagulation action of Dabigatran, producing immediate clotting of the blood in the loop.

Example 3 Anticoagulation Effect of Dabigatran in the Cardiopulmonary Bypass Circuit Simulation Goal: Intention of this study was to evaluate the dose-dependent anticoagulation properties of Dabigatran at 5000, 7500 and 10000 ng/ml in Cardiopulmonary bypass circuit (arterio-venous loop) with the tight temperature, blood gases (pO2, pCO2) and electrolytes (Na, K, Ca, CL) control.

Methods: 5 mg of Dabigatran was initially dissolved in 300 μl of 0.075 M HCL, followed by diluting with 1 ml of 20% Dimethylacetamide in $H_2O$ to get 3840 μg/ml stock according to steps 1-3 below. From the stock, 195 μl, 292.5 μl and 390 μl of Dabigatran were added to 150 ml of citrated blood to create the final concentrations 5000 ng/ml, 7500 ng/ml and 10000 ng/ml according to steps 4-5 below.
- Step 1 (acid dilution): Add 7500 of 1M HCl into 9.25 ml $H_2O$ to make 0.075M HCl;
- Step 2 (solvent dilution): Add 2.5 ml DMA (ACROS Organics, 99+%, extra pure, Catalog No. AC181070010) into 10 ml $H_2O$ to make fresh 20% DMA;
- Step 2 (initial Dabigatran stock solution): Dissolve 5 mg of Dabigatran (MW=471.51, Clearsynth, Catalog No. CS-O-03403) in 3000 of 0.075M HCl and mix the resulting solution well (Solution 1);
- Step 3 (final Dabigatran stock solution): Add 1 ml of 20% DMA into 300 μl of Solution 1 to obtain a 3840 μg/ml stock of Dabigatrane (Solution 2); Solution 2 should have pH ≈3.5 at room temperature;
- Step 4 (blood preparation): In 100 ml of fresh whole human blood, add Na-Citrate 15 ml, 25% Albumine (Human) 15 ml, and PlasmaLyte-A 20 ml. The total volume is 150 ml ("citrated blood"). Load 150 ml of the citrated blood into the Cardiopulmonary bypass circuit and incubate at 37° C. with a constant perfusion of 5% $CO_2$+95% $O_2$.
- Step 5 (final Dabigatran injection): Add 1950 of Solution 2 into 150 ml of citrated blood to obtain 5000 ng/ml final Dabigatran;
Add 292.50 of Solution 2 into 150 ml of citrated blood to obtain 7500 ng/ml final Dabigatran;
Add 3900 of Solution 2 into 150 ml of citrated blood to obtain 10000 ng/ml final Dabigatran;
Incubate the Dabigatran-blood mixtures for 5 min.
- Step 6 ($CaCl_2$) injection): Add 1 ml 124 μl $CaCl_2$ (from 1M stock solution) into 150 ml of citrated blood to override citrate activity. The final $CaCl_2$ concentration is 7.5 mM.

Results: Mass Spectrometry showed that plasma levels of Dabigatran remain stable during the whole duration of the experimental procedure. Electron microscopy of segments of the arterial filter showed fibrin deposition at the lower level of Dabigatran (5000 ng/ml); however at the higher levels (7500 and 10000 ng/ml) Dabigatran prevented deposition of fibrin with equal efficacy to heparin. Heparin was utilized as a positive anticoagulation control.

The results of this series of experiments demonstrate (i) dabigatran may be formulated for parenteral administration in an acceptable concentration and pH; (ii) dabigatran at high concentration inhibits clot formation in a dose-dependent fashion; (iii) high-concentration dabigatran is easily reversed with high concentration Idarucizumab; and (iv) high-concentration dabigatran maintains the fluidity of human blood in in vitro simulations approximating those of clinical cardiopulmonary bypass.

Example 4 Anticoagulation Effects of Different Dabigatran Stocks in Cardiopulmonary Bypass Circuit Simulation In this example, additional dabigatran-containing solutions were made and tested. To that end, dabigatran was dissolved in either DMSO (0.075M HCl+50% DMSO), DMA (0.075M HCl+20% DMA) or NMP (0.075M HCl+50% NMP) in the manner described above.

A first dabigatran stock in HCl/DMSO (pH 3.2) was made by dissolving 5 mg dabigatran in 300 ul of 0.1 M HCl, followed by dilution in 50% DMSO up to 10.4 ml. The stock had 480 ug/ml dabigatran. Then, 5 ul of the stock was mixed with 1 ml of citrated blood to obtain a final concentration of 2400 ng/ml.

A second dabigatran stock in HCl/DMSO (pH 3.5) was made by dissolving 5 mg dabigatran in 300 ul of 0.075 M HCl, followed by dilution in 50% DMSO up to 10.4 ml to arrive at the concentration of 480 ug/ml. Then, 5 ul of the stock was mixed with 1 ml of citrated blood to obtain a final concentration of 2400 ng/ml.

A third dabigatran stock in HCl/DMA (pH 3.5) was made by dissolving 5 mg dabigatran in 300 ul of 0.075 M HCl, followed by dilution in 20% DMA up to 10.4 ml to arrive at the concentration of 480 ug/ml. Then, 5 ul of the stock was mixed with 1 ml of citrated blood to obtain a final concentration of 2400 ng/ml.

A fourth dabigatran stock in HCl/NMP (pH 3.8) was made by dissolving 5 mg dabigatran in 300 ul of 0.075 M HCl, followed by dilution in 20% NMP up to 10.4 ml to arrive at the concentration of 480 ug/ml. Then, 5 ul of the stock was mixed with 1 ml of citrated blood to obtain a final concentration of 2400 ng/ml.

Figure 4:
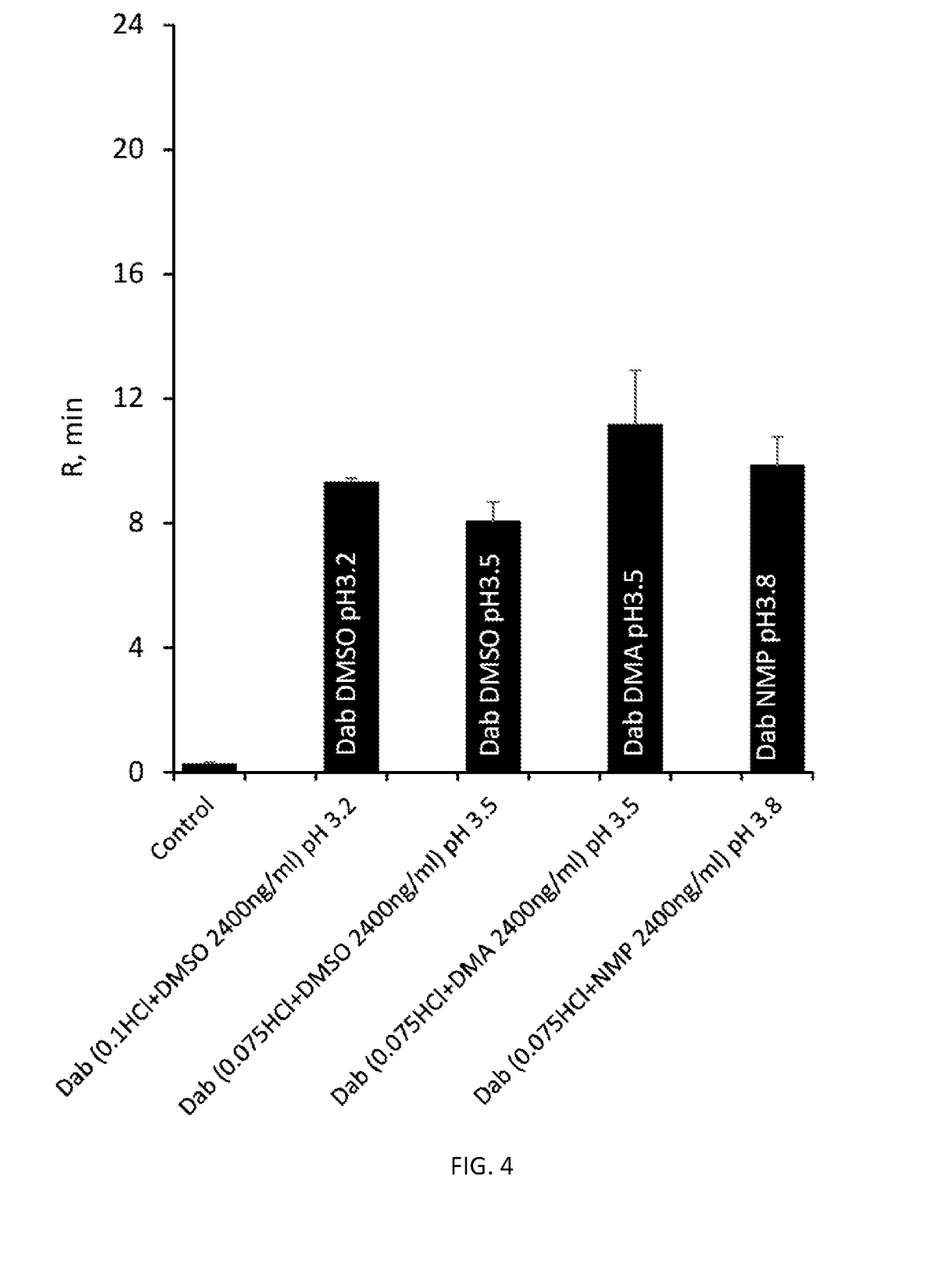
FIG. 4 is diagrams showing clotting times (R) measured by TEG in the presence of dabigatran prepared from different stock solutions.

Each of the dabibatran-containing blood sample described above was examined for clotting time R measured by TEG in the manner described above. The results are shown in FIG. 4. The results indicate that all stocks were effective in inhibiting blood clotting.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. A method for managing or inhibiting blood coagulation during a procedure in a subject, comprising administering parenterally to the subject or the blood thereof an effective amount of dabigatran so that the blood dabigatran concentration is about 500 ng/ml to about 30,000 ng/ml, and wherein the procedure is a cardiopulmonary bypass procedure or an extracorporeal circulation procedure.

2. The method of claim 1, wherein the blood dabigatran concentration is about 2,400 ng/ml to about 20,000 ng/ml.

3. The method of claim 2, wherein the blood dabigatran concentration is about 9,600 ng/ml to about 20,000 ng/ml.

4. The method of claim 1, wherein the administering step comprises administering to the subject or the blood thereof a liquid pharmaceutical composition comprising about 2 µg/ml to about 20 mg/ml dabigatran or a pharmaceutically acceptable salt thereof.

5. The method of claim 1, further comprising conducting the cardiopulmonary bypass or extracorporeal circulation procedure, wherein the dabigatran is administered to the subject during the procedure.

6. The method of claim 1, wherein the dabigatran is administered to a prime volume of the subject in vitro in a heart-lung machine for the procedure.

7. The method of claim 1, further comprising administering to the subject an effective amount of a second anticoagulant.

8. The method of claim 7, wherein the second anticoagulant is a direct-acting Factor Xa inhibitor.

9. The method of claim 8, wherein the direct-acting Factor Xa inhibitor is rivaroxaban, apixaban, fondaparinux, edoxaban, or betrixaban.

10. The method of claim 1, further comprising administering to the subject an effective amount of an antibody that specifically binds to the dabigatran or a pharmaceutically acceptable salt thereof.

11. The method of claim 10, wherein the antibody comprises idarucizumab.

12. The method of claim 4, wherein the blood dabigatran concentration is about 4,000 ng/ml to about 10,000 ng/ml.

13. The method of claim 12, wherein the blood dabigatran concentration is about 6,000 ng/ml to about 9,000 ng/ml.

* * * * *